United States Patent
Mino et al.

(10) Patent No.: US 12,065,571 B2
(45) Date of Patent: Aug. 20, 2024

(54) PIGMENT COMPOSED OF PARTICLES CONTAINING CALCIUM-TITANIUM COMPOSITE OXIDE AS MAIN COMPONENT, AND USE THEREOF

(71) Applicant: TITAN KOGYO KABUSHIKI KAISHA, Yamaguchi (JP)

(72) Inventors: Wataru Mino, Yamaguchi (JP); Naotaka Shimomura, Yamaguchi (JP); Chihiro Nada, Yamaguchi (JP); Nami Matsushima, Yamaguchi (JP)

(73) Assignee: TITAN KOGYO KABUSHIKI KAISHA, Yamaguchi (JP)

( * ) Notice: Subject to any disclaimer, the term of this patent is extended or adjusted under 35 U.S.C. 154(b) by 0 days.

(21) Appl. No.: 18/245,821

(22) PCT Filed: Aug. 27, 2021

(86) PCT No.: PCT/JP2021/031496
§ 371 (c)(1),
(2) Date: Mar. 17, 2023

(87) PCT Pub. No.: WO2022/059460
PCT Pub. Date: Mar. 24, 2022

(65) Prior Publication Data
US 2023/0340271 A1    Oct. 26, 2023

(30) Foreign Application Priority Data
Sep. 18, 2020   (JP) .................. 2020-157588

(51) Int. Cl.
*C09C 1/36*    (2006.01)
*A61K 8/02*    (2006.01)
(Continued)

(52) U.S. Cl.
CPC .............. *C09C 1/36* (2013.01); *A61K 8/025* (2013.01); *A61K 8/29* (2013.01); *A61Q 19/00* (2013.01);
(Continued)

(58) Field of Classification Search
CPC ...................... C09C 1/36; C01G 23/003–006
See application file for complete search history.

(56) References Cited

U.S. PATENT DOCUMENTS

| | | |
|---|---|---|
| 10,703,913 B2 | 7/2020 | Hata |
| 2009/0060856 A1 | 3/2009 | Katsuyama et al. |

FOREIGN PATENT DOCUMENTS

| | | |
|---|---|---|
| CN | 104477976 A | 4/2015 |
| CN | 108408766 A | 8/2018 |

(Continued)

OTHER PUBLICATIONS

Machine translation EP 0493241 (Year: 2023).*
(Continued)

*Primary Examiner* — Alexandre F Ferre
(74) *Attorney, Agent, or Firm* — COZEN O'CONNOR

(57) ABSTRACT

The pigment is composed of particles having a lattice constant a of 5.4700-5.5100 Å and containing a calcium-titanium composite oxide as a main component. The pigment selectively transmit light in a warm-color range, and can be used as an alternative material for titanium oxide. This pigment can be used for a cosmetic, for example.

13 Claims, 3 Drawing Sheets

(51) Int. Cl.
- *A61K 8/29* (2006.01)
- *A61Q 19/00* (2006.01)
- *C01G 23/00* (2006.01)
- *C08J 5/18* (2006.01)
- *C08K 3/22* (2006.01)
- *C08K 7/18* (2006.01)
- *C08K 9/00* (2006.01)
- *C09D 7/40* (2018.01)
- *C09D 7/62* (2018.01)
- *C09D 11/037* (2014.01)

(52) U.S. Cl.
CPC ............. *C01G 23/006* (2013.01); *C08J 5/18* (2013.01); *C08K 3/22* (2013.01); *C08K 7/18* (2013.01); *C08K 9/00* (2013.01); *C09D 7/62* (2018.01); *C09D 7/70* (2018.01); *C09D 11/037* (2013.01); *A61K 2800/10* (2013.01); *A61K 2800/43* (2013.01); *C01P 2002/60* (2013.01); *C01P 2002/72* (2013.01); *C01P 2002/76* (2013.01); *C01P 2002/78* (2013.01); *C01P 2004/04* (2013.01); *C01P 2004/32* (2013.01); *C01P 2004/39* (2013.01); *C01P 2004/80* (2013.01); *C01P 2006/12* (2013.01); *C08K 2003/2237* (2013.01); *C08K 2201/006* (2013.01)

(56) References Cited

FOREIGN PATENT DOCUMENTS

| | | | | |
|---|---|---|---|---|
| EP | 493241 | A1 * | 7/1992 | ............. C01B 13/14 |
| JP | 5-339122 | A | 12/1993 | |
| JP | H05-339121 | A | 12/1993 | |
| JP | 8-310913 | A | 11/1996 | |
| JP | 2001-163731 | A | 6/2001 | |
| JP | 3464564 | B2 | 11/2003 | |
| JP | 2005-112665 | A | 4/2005 | |
| JP | 2008-297142 | A | 12/2008 | |
| JP | 4684970 | B2 | 5/2011 | |
| JP | 5363696 | B2 | 12/2013 | |
| JP | 6258462 | B2 | 1/2018 | |
| JP | 2020-11857 | A | 1/2020 | |
| WO | WO-2018079487 | A1 * | 5/2018 | ........... C09C 1/0081 |

OTHER PUBLICATIONS

Machine translation WO201807949487 (Year: 2023).*
International Application No. PCT/JP2021/031496, International Search Report mailed Nov. 16, 2021, 6 pages.

* cited by examiner

PIGMENT COMPOSED OF PARTICLES CONTAINING CALCIUM-TITANIUM COMPOSITE OXIDE AS MAIN COMPONENT, AND USE THEREOF

This application is a national stage application of PCT/JP2021/031496 filed on Aug. 27, 2021, which claims priority to Japanese App. No. 2020-157588, filed on Sep. 18, 2020, the entirety of which is incorporated herein by reference.

TECHNICAL FIELD

The present invention relates to a pigment composed of particles containing a calcium-titanium composite oxide as a main component, and particularly to the pigment having a warm color light-transmitting effect.

BACKGROUND ART

Conventionally, make-up cosmetics, such as a foundation, contain colorants such as titanium oxide pigments, which have a large tinting strength, as well as other colorants such as inorganic pigments and organic pigments in order to change skin tone for the purpose of covering up redness, dullness, spots, freckles, and the like of the skin to give a uniform and beautiful skin appearance.

As the titanium oxide, a pigment having a high tinting strength and high concealing strength is typically used to give a uniform skin tone. As the titanium oxide, pigment grade titanium oxide having a rutile-type crystal structure with a primary particle size of 0.1 µm or more and 0.3 µm or less is widely used. However, when a foundation containing such titanium oxide is applied to the skin as a cosmetic, the intensity of scattered white light tends to be too strong, and thus the finish of the makeup tends to look pale and unnatural, resulting in the problem of so-called "white cast".

One way to prevent the white cast phenomenon is to use a rutile-type titanium oxide having a specific shape to balance the tinting strength and concealing strength with the intensity of the scattered white light. For example, Japanese Patent No. 4,684,970 (Patent Literature 1) describes blending, into a cosmetic, an aggregate of fan-shaped rutile titanium oxide particles in which rod-shaped primary particles are aggregated and/or bound. Further, Japanese Patent No. 6258462 (Patent Literature 2) describes blending, into a cosmetic, a rutile-type titanium dioxide powder obtained by baking rutile-type titanium dioxide having needle-like projections on the particle surface.

Another way to prevent the white cast phenomenon is to use a scattering of light in a warm color range inside a skin. Japanese Patent No. 5,363,696 (Patent Literature 3) describes a study focused on a light propagating inside a bare skin. Specifically, it is described that, in a light scattering medium such as a skin, a part of the light irradiated on the skin penetrates into the interior, and is reflected by internal scattering bodies, and is therefore emitted even from sites different from the irradiated sites; and that use of a colorant having a low absorptivity of light in the wavelength range of 630 nm to 700 nm in a skin cosmetic provides a distribution of the emission sites similar to that of bare skin, resulting in a natural skin texture.

However, in recent years, there has been a growing movement, mainly in Europe, to reduce the amount of titanium(IV) oxide, including rutile-type titanium oxide, and to use substitute materials, because of its possibility of a health hazard. Japanese Patent Application Laid-Open No. H05-339121 (Literature 4) proposes using compounds having a perovskite crystal structure, such as calcium titanate, strontium titanate, barium titanate, calcium zirconate, and strontium zirconate, as pigments other than rutile-type titanium oxide. Japanese Patent No. 3464564 (Patent Literature 5) also describes an ultraviolet protection cosmetic using particles of a complex oxide having a perovskite structure or a solid solution thereof.

CITATION LIST

Patent Literature

PTL 1: Japanese Patent No. 4684970
PTL 2: Japanese Patent No. 6258462
PTL 3: Japanese Patent No. 5363696
PTL 4: Japanese Patent Laid-Open No. H05-339121
PTL 5: Japanese Patent No. 3464564

SUMMARY OF INVENTION

Technical Problem

However, Patent Literature 4 discusses only lubricity, adhesion, and covering strength, and does not take into account the white cast phenomenon. In addition, Patent Literature 4 merely describes that a powder composed of particles made of a compound having a perovskite crystal structure, having an average particle size in the range of 0.05 to 15 µm, and having an equiaxed shape is added to a cosmetic, and it does not describe a specific method of producing such a powder. In addition, although Patent Literature 5 describes that a complex oxide powder represented by $CaTiO_3$ is synthesized, it does not describe a specific example in which this powder is added to a cosmetic. Moreover, although the ultraviolet-protecting effect, safety, and stability of a cosmetic containing a complex oxide having a perovskite structure are described, countermeasures against the white cast phenomenon are not studied.

Although the development of substitutes for titanium oxide is progressing, the development of cosmetics that achieve a natural finish is still in progress. In particular, there has not been obtained a substitute for titanium oxide that utilizes an effect of selectively transmitting light in a warm color range.

An object of the present invention is to provide a pigment that selectively transmits light in a warm color range and that can be used as a substitute for titanium oxide.

Solution to Problem

The present inventors have focused on calcium-titanium composite oxides as a substitute for titanium oxide, and as a result of intensive studies, have found that a pigment composed of particles containing a calcium-titanium composite oxide with a specific crystal structure as a main component selectively transmits light in a warm color range.

The present invention includes the following, but is not limited thereto.

[1] A pigment composed of particles comprising a calcium-titanium composite oxide as a main component, wherein a lattice constant a of the pigment is in a range of 5.4700 Å or more and 5.5100 Å or less.

[2] The pigment according to [1], wherein the calcium-titanium composite oxide is a calcium-titanium composite oxide having an orthorhombic crystal system.

[3] The pigment according to [1] or [2], wherein, when the pigment is measured in X-ray diffractometry, and when a height of a diffraction line of a (1 2 1) plane appearing in a range of a diffraction angle of 32.50° or more and 33.50° or less is defined as 100.0, a height of a diffraction line of a (2 0 2) plane appearing in a range of a diffraction angle of 46.75° or more and 47.75° or less is 50.0 or less.

[4] The pigment according to any one of [1] to [3], wherein the pigment has a specific surface area of 3.0 m$^2$/g or more.

[5] The pigment according to any one of [1] to [4], wherein, when the pigment is measured in X-ray diffractometry, and when an integrated diffraction intensity of a (1 2 1) plane appearing in a range of a diffraction angle of 32.50° or more and 33.50° or less is defined as 100.0, a diffraction line having an integrated diffraction intensity greater than 12.00 does not appear in a range of a diffraction angle of 24.75° or more and 28.00° or less.

[6] The pigment according to any one of [1] to [5], wherein a coating layer of an inorganic substance and/or an organic substance is present on at least a part of a surface of the particles.

[7] The pigment according to any one of [1] to [6], wherein the particles have an approximately spherical shape.

[8] The pigment according to any one of [1] to [6], wherein the particles have a rectangular parallelepiped shape.

[9] The pigment according to any one of [1] to [8], wherein a crystallite size of the particles is in a range of 250 Å or more and 600 Å or less.

[10] A cosmetic comprising the pigment according to any one of [1] to [9].

[11] A film composition comprising the pigment according to any one of [1] to [9].

[12] A resin composition comprising the pigment according to any one of [1] to [9].

[13] A paint comprising the pigment according to any one of [1] to [9].

[14] An ink comprising the pigment according to any one of [1] to [9].

Advantageous Effects of Invention

The pigment obtained by the present invention, which consists of particles containing a calcium-titanium composite oxide as a main component, can selectively transmit light in a warm color range.

When the pigment obtained by the present invention, which consists of particles containing a calcium-titanium composite oxide as a main component, is used as a material, in particular, for a cosmetic, such as a foundation, that is applied to a skin, a transmitted light in a warm color range scatters inside the skin, thereby enabling a natural finish.

The pigment obtained by the present invention can also be used as a substitute for titanium oxide. Since the calcium-titanium composite oxide used in the pigment of the present invention has a UV-blocking effect equivalent to that of titanium oxide, it can be used in sunscreen creams and the like.

The pigment obtained by the present invention can be used in a wide range of applications in fields other than cosmetics by utilizing its ability to transmit light in a warm color range. Examples of such applications include, but are not limited to, adding to a transparent material for use in optical equipment components, adding to a resin to form a resin composition having a warm color light-transmitting effect, and adding to a paint for use in residential paints.

DESCRIPTION OF EMBODIMENTS

Figure 1:
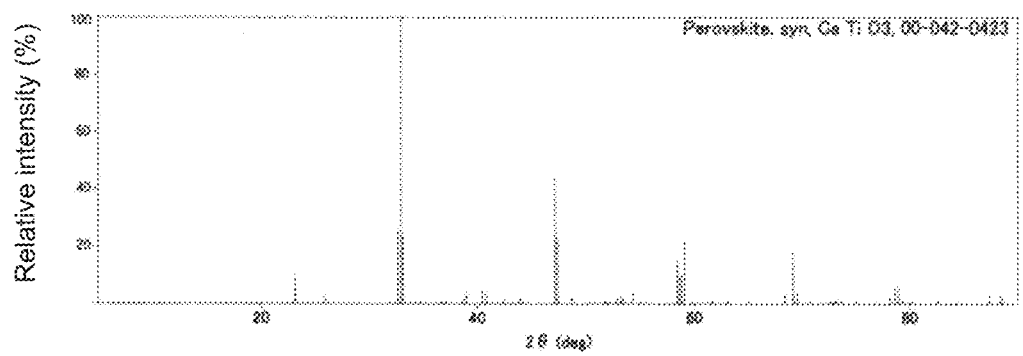
FIG. 1 is an X-ray diffraction pattern of a calcium-titanium composite oxide represented by the chemical formula $CaTiO_3$, which is registered in a PDF card.
Figure 2:
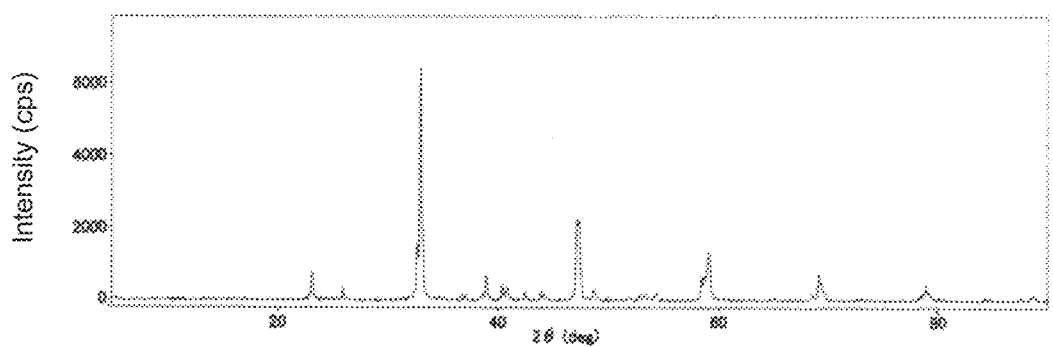
FIG. 2 is an X-ray diffraction pattern of a pigment composed of particles having the calcium-titanium composite oxide as a main component obtained in Example 4.
Figure 3:
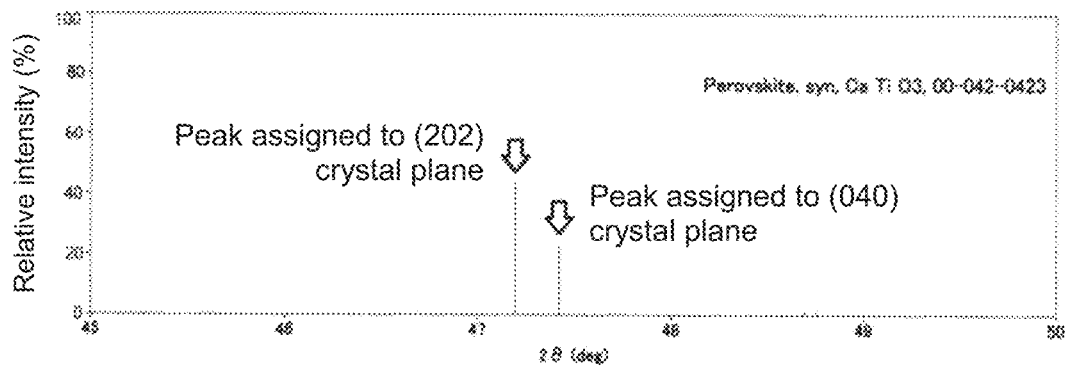
FIG. 3 shows a portion in a diffraction angle 2θ of 45.0° or more and 50.0° or less of the X-ray diffraction pattern of a calcium-titanium composite oxide represented by the chemical formula $CaTiO_3$, which is registered in a PDF card.
Figure 4:
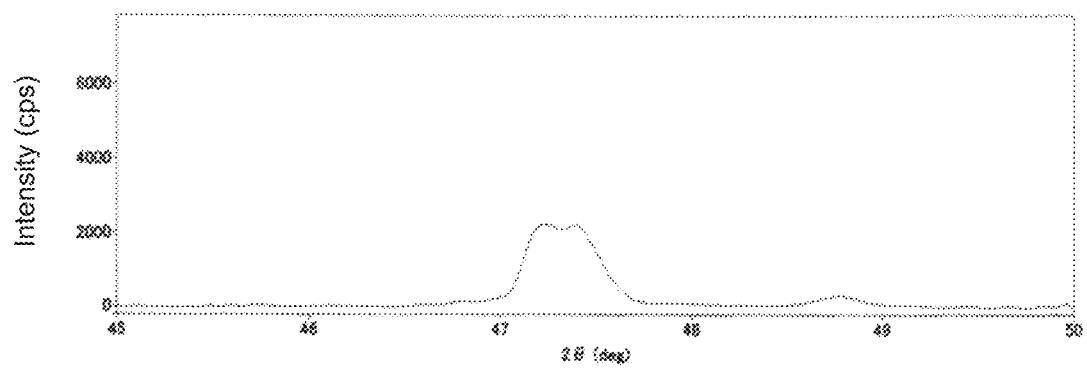
FIG. 4 shows a portion in a diffraction angle 2θ of 45.0° or more and 50.0° or less of the X-ray diffraction pattern of the pigment obtained in Example 4.

The present invention relates to a pigment composed of particles containing a calcium-titanium composite oxide as a main ingredient, and having a lattice constant a of 5.4700 Å or more and 5.5100 Å or less. "Pigment composed of (or consisting of) particles containing a calcium-titanium composite oxide as a main component (or a main ingredient)" means that the individual particles constituting the pigment are mainly calcium-titanium composite oxide particles. Specifically, this means that 850 g/kg or more, and preferably 900 g/kg or more, of the individual particles constituting the pigment are calcium-titanium composite oxide particles. In addition to the calcium-titanium composite oxide, the individual particles constituting the pigment of the present invention may include unreacted substances from a synthesis reaction of the calcium-titanium composite oxide, unavoidable impurities derived from raw materials, and inorganic substances and/or organic substances derived from a coating layer.

The calcium-titanium composite oxide, which is the main component of the particles constituting the pigment of the present invention, is preferably a calcium-titanium composite oxide having an orthorhombic crystal system. "Calcium-titanium composite oxide having an orthorhombic crystal system" refers to a calcium-titanium composite oxide in which the angles between two different crystal axes are all 90°.

The pigment of the present invention, which includes particles containing a calcium-titanium composite oxide as a main ingredient, is characterized by having a large "lattice constant a" when a space group of the perovskite crystal structure is Pnma (62), as compared to a general calcium-titanium composite oxide represented by a chemical formula $CaTiO_3$. Although it is not clear why light in a warm color range is selectively transmitted when the lattice constant a increases, the reason is probably considered to be as follows. When the lattice constant a increases, the arrangement of the crystals is disturbed, and particularly light in a low-wavelength region tends to attenuate. As a result, light in a long wavelength region (that is, light in a warm color range) is selectively transmitted. The lattice constant a is preferably 5.4700 Å or more, more preferably 5.4725 Å or more, and further preferably 5.4750 Å or more. On the other hand, when the lattice constant a is further increased, a lattice constant b becomes closer to the lattice constant a, and a regularity of a crystal packing increases again. As a result, the function of selectively transmitting light in a warm color range is lost. The lattice constant a is preferably 5.5100 Å or less, more preferably 5.5050 Å or less, and further preferably 5.5030 Å or less.

In the pigment of the present invention, due to its larger lattice constant a than that of a general calcium-titanium composite oxide represented by a chemical formula $CaTiO_3$, a position of a diffraction line of each crystal plane measured by a powder method in an X-ray diffractometry shifts. Specifically, a diffraction line assigned to a crystal plane with the Miller index (202) shifts to a lower angle side. On the other hand, a diffraction line assigned to a crystal plane with the Miller index (0 4 0) does not shift. As a result, in a range of the diffraction angle 2θ of 46.75° or more and 47.75° or less, the diffraction lines of the (2 0 2) plane and the (0 4 0) plane, which are generally observed overlapping at the same position, clearly separate, and the peak height of the diffraction lines is lower than before the separation. Specifically, in the present invention, when a height of a diffraction line of a (1 2 1) plane appearing in a range of a diffraction angle 2θ of 32.50° or more and 33.50° or less, which is the largest diffraction line of the calcium-titanium composite oxide, is defined as 100.0, the height of the diffraction line of the (2 0 2) plane (hereinafter, referred to as "XRD diffraction line height ratio") is preferably 50.0 or less, more preferably 48.0 or less, and further preferably 46.0 or less.

The pigment of the present invention preferably has a large specific surface area. Although the reason for this is not clear, it is probably considered to be as follows. On the surface of the particles containing calcium-titanium composite oxide as a main component used in the present invention, asperities and cracks are present. Whereas short-wavelength light tends to be scattered by these asperities and cracks, long-wavelength light in a warm color range is not greatly affected. Therefore, particles with more asperities and cracks tend to more selectively transmit light in the warm color range. The specific surface area is preferably 3.0 $m^2/g$ or more, and more preferably 3.5 $m^2/g$ or more. Although there is no particular upper limit to the specific surface area of the pigment of the present invention, a specific surface area of 200 $m^2/g$ or less is desirable because this brings about non-excessive oil absorption and therefore advantages such as easier control of the properties of the cosmetic can be obtained.

It is desirable that the pigment of the present invention, which is composed of particles containing a calcium-titanium composite oxide as a main component, should have a small titanium oxide content because the pigment of the present invention may be used as a substitute material for titanium oxide in cosmetics. To accurately calculate the content of titanium oxide in the calcium-titanium composite oxide, it is necessary to mix the calcium-titanium composite oxide of the present invention and titanium oxide, and subject the resultant mixture to X-ray diffractometry using a powder method to create a calibration curve. However, this method is time consuming and costly. Therefore, in a method for more easily confirming that the content of titanium oxide is small, an integrated diffraction intensity of a diffraction line appearing at 24.75° or more and 28.00° or less, which has the highest integrated diffraction intensity of rutile, anatase, and brookite titanium oxides, is compared with an integrated diffraction intensity of a diffraction line of the (1 2 1) plane appearing at 32.50° or more and 33.50° or less, which is the highest integrated diffraction intensity of calcium-titanium composite oxide, in X-ray diffractometry by a powder method. In the present invention, in view of a small titanium oxide content, when the integrated diffraction intensity of the (1 2 1) plane appearing at 32.50° or more and 33.50° or less is defined as 100.0, it is preferable that a diffraction line having an integrated diffraction intensity greater than 12.00 should not appear in the range of 24.75° or more and 28.00° or less. More preferably, when the integrated diffraction intensity of the (1 2 1) plane appearing at 32.50° or more and 33.50° or less is defined as 100.0, the ratio of the integrated diffraction intensity of the diffraction line appearing at 24.75° or more and 28.00° or less (hereinafter, referred to as "XRD titanium oxide integrated diffraction intensity") is 11.00 or less, and further preferably 8.50 or less. A diffraction line of a (1 1 1) plane of the calcium-titanium composite oxide appears at 24.75° or more and 28.00° or less, and the integrated diffraction intensity of the diffraction line of the (1 1 1) plane is about 3 when the integrated intensity of the (1 2 1) plane is defined as 100.0. Accordingly, the integrated diffraction intensity does not become zero even if no titanium oxide is present at all.

Figure 5:
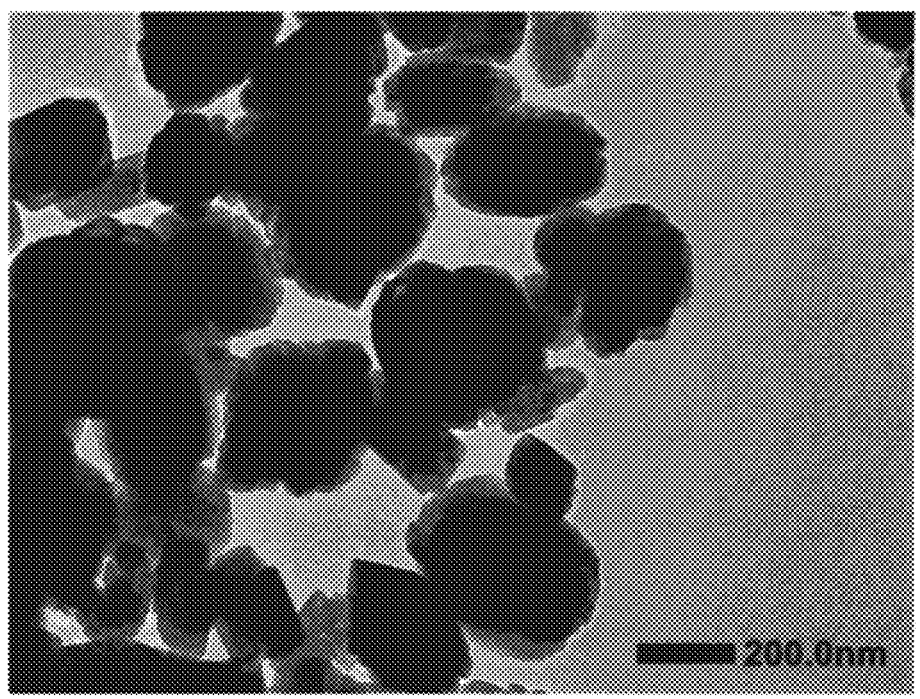
FIG. 5 is a transmission electron micrograph of the pigment obtained in Example 4.
Figure 6:
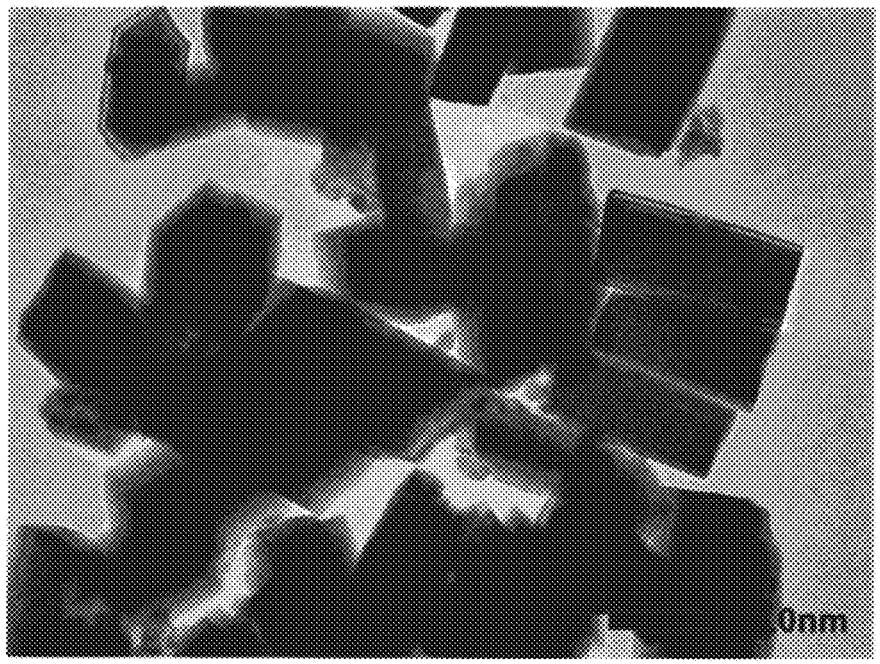
FIG. 6 is a transmission electron micrograph of the pigment obtained in Example 1.

In the pigment obtained by the present invention, the particles may have an approximately spherical shape or have a rectangular parallelepiped shape. "Approximately spherical" means that, as illustrated in FIG. 5, the primary particles or secondary particles are crystals that have grown isotropically or form aggregates isotropically, have an irregular outer shape or an outer shape similar to a sphere, and have a degree of circularity of 0.790 or more as calculated by the method described later. For example, "approximately spherical" does not include a rectangular parallelepiped shape like that shown in FIG. 6, an elongated needle shape, or a shape like a sea urchin that has protrusions with a length equal to or longer than the diameter of the central part. "Rectangular parallelepiped" means that, as illustrated in FIG. 6, the primary particles or secondary particles have an outer shape close to a rectangular parallelepiped as a result of crystal growth preferential in a specific uniaxial direction than in the other two axes or as a result of aggregates preferentially formed in a specific uniaxial direction than in the other two axes, and have a degree of circularity calculated by the method described later of less than 0.790. "Rectangular parallelepiped" does not have to refer to a perfect rectangular parallelepiped (in which all six faces are formed by rectangles or squares). Further, the shape of the cross-section of the particle perpendicular to the major axis direction does not need to be rectangular or square, and the cross-sectional shape of all the cross-sections need not be the same shape.

"Particles have an approximately spherical shape" and "particles have a rectangular parallelepiped shape" mean that 80% by number or more, and preferably 85% by number or more, of the particles constituting the pigment of the present invention are approximately spherical and rectangular parallelepiped, respectively.

If the calcium-titanium composite oxide, which is the main component of the particles constituting the pigment of the present invention, has a small crystallite size, crystal growth generally tends to be insufficient and properties tend to be unstable. Therefore, the crystallite size of the particles constituting the pigment, as determined by X-ray diffraction, is preferably 250 Å or more, and more preferably 300 Å or more. In view of tactile sensation when used in cosmetics, the upper limit of the crystallite size is preferably 600 Å or less. The crystallite size can be measured by the method described later.

The pigment of the present invention preferably has a smaller particle size distribution. If the particle size distribution is large, the particles are non-uniform so that lubricity tends to be poor when used for a cosmetic. In view of lubricity when used in cosmetics, the particle size distribution calculated by the method described later is preferably 10.00 or less, more preferably 8.00 or less, and further preferably 5.00 or less.

The pigment of the present invention preferably has good lubricity. Pigments having a narrow particle size distribution tend to have good lubricity. Further, in general, among rectangular parallelepiped particles and approximately spherical particles, approximately spherical particles tend to have better lubricity. Therefore, in view of lubricity, it is preferable that the particles should have a large degree of circularity.

The pigment of the present invention preferably has a warm color light-transmitting effect of 0.56 or more calculated by the method described later. When the warm color light-transmitting effect is 0.56 or more, reflection of light in a warm color range inside the skin is sufficient when the pigment is used in cosmetics, and a natural finish can thus be obtained. Although there is no particular upper limit for the warm color light-transmitting effect, the theoretical maximum value of the warm-color light-transmitting effect calculated by the evaluation method used in the present invention is 1.00.

The color of the pigment of the present invention is not particularly limited. However, since the pigment of the present invention may be used as a substitute for titanium oxide, it is preferably white like titanium oxide.

The pigment of the present invention may have a coating layer made of an inorganic material on the surface of the particles in order to impart hydrophobicity, optical properties, and the like. A coating layer made of an organic substance may be present. There may be two or more coating layers, or an inorganic coating layer and an organic coating layer may both be included.

An example of the method for manufacturing the pigment of the present invention is shown below. However, the method for manufacturing the pigment of the present invention is not limited to the following.

The pigment of the present invention, which includes particles containing a calcium-titanium composite oxide as a main ingredient, can be obtained by a method called a normal pressure heating reaction method, which includes synthesizing a calcium-titanium composite oxide by mixing, at normal pressure, an acid deflocculant of a hydrolyzate of a titanium compound, a water-soluble compound containing calcium, and an alkali, and heating the mixture to 70° C. or higher and 100° C. or lower. An exemplary acid deflocculant of a hydrolyzate of a titanium compound is metatitanic acid obtained by a method called a sulfuric acid method. After obtaining the calcium-titanium composite oxide by the above method, it is preferable to carry out a calcium removal treatment.

(Sulfuric Acid Method)

Metatitanic acid represented by a chemical formula TiO(OH)$_2$ can be obtained by dissolving ilmenite ore with concentrated sulfuric acid and removing the resulting iron sulfate component.

(Normal Pressure Heating Reaction Method)

Examples of the acid deflocculant of a hydrolyzate of a titanium compound include metatitanic acid. As the metatitanic acid, it is preferable to use one obtained by using a compound having a sulfur content, in terms of SO$_3$, of 15 g/kg or less, and preferably 10 g/kg or less, as the hydrolyzate of a titanium compound, and deflocculating the hydrolyzate by adjusting the pH of the hydrolyzate to 0.8 or more and 1.5 or less using hydrochloric acid. This makes it possible to obtain calcium-titanium composite oxide particles having a small particle size distribution. If the sulfur in the metatitanic acid exceeds 15 g/kg in terms of SO$_3$, deflocculation may not progress. Nitric acid, hydrogen bromide, hydrogen iodide, formic acid, acetic acid or the like can also be used instead of hydrochloric acid. Further, instead of the acid deflocculant of a hydrolyzate of a titanium compound, a product obtained by neutralizing the same deflocculant with an alkali can be used.

As the alkali to be mixed with the acid deflocculant of a hydrolyzate of a titanium compound, caustic alkali can be used, and sodium hydroxide is particularly preferable. The alkali concentration in the mixture in the normal pressure heating reaction method is preferably 0.1 mol/L or more, and more preferably in the range of 0.5 mol/L or more and 3.6 mol/L or less.

Examples of the factors influencing the crystallinity and particle size of the pigment composed of particles containing a calcium-titanium composite oxide as a main component obtained by the normal pressure heating reaction method include concentrations and mixing ratios of the raw materials, the alkali concentration, the reaction temperature, and additives, etc. The mixing ratio between the acid deflocculant of a hydrolyzate of a titanium compound and the water-soluble compound containing calcium is preferably such that the ratio of the amount of calcium (Ca element) to the amount of titanium (Ti element) is 1.00 or more and 1.60 or less, and more preferably 1.10 or more and 1.50 or less. The acid deflocculant of a hydrolyzate of a titanium compound has a low solubility in water; accordingly, when the amount of calcium is less than the amount of titanium, the reaction product tends to contain not only calcium-titanium composite oxide particles, but also unreacted titanium oxide. The concentration of the acid deflocculant of a hydrolyzate of a titanium compound in the mixture in the normal pressure heating reaction method is preferably, in terms of Ti, 0.5 mol/L or more and 1.5 mol/L or less, and more preferably 0.7 mol/L or more and 1.4 mol/L or less.

The higher the temperature during the reaction, the better the crystallinity of the product to be obtained. However, at a temperature exceeding 100° C., a pressure vessel is required for the reaction. Accordingly, for practical use, the range of 70° C. or higher and 100° C. or lower is suitable, and the range of 70° C. or higher and lower than 100° C. is also acceptable.

To obtain the particles having a substantially approximately spherical, one or more sugars selected from monosaccharides or disaccharides such as glucose and maltose may be added as additives during the normal pressure heating reaction. When any of sugars as described above are added, the total concentration thereof is preferably 0.0115 mole or more and 0.0195 mole or less, per mole of calcium added during the normal pressure heating reaction. When the concentration is less than 0.115 mol/mol, the particles may not become approximately spherical, and when the concentration is more than 0.195 mol/mol, titanium oxide tends to remain. Further, in general, the particles tend to be small when the amount of sugar added is large. In the case of using as a cosmetic, it is preferable that the particles should not be too small, and so from this perspective the concentration of the sugar(s) to be added is preferably not more than 0.195 mol/mol.

One or more compounds selected from aliphatic hydroxy acid compounds such as citric acid and isocitric acid may be added during the normal pressure heating reaction. Adding an aliphatic hydroxy acid compound increases the aspect ratio of the particles. The amount of the aliphatic hydroxy acid added is preferably 0.0180 mole or less per mole of calcium added during the normal pressure heating reaction.

(Calcium Removal Treatment)

After synthesizing the calcium-titanium composite oxide by the normal pressure heating reaction, it is preferable to carry out calcium removal treatment to prevent unreacted calcium from remaining and interfering with the surface treatment. The calcium removal treatment includes adjusting the pH to 2.5 or more and 7.0 or less, and more preferably to a pH of 4.5 or more and 6.0 or less, using hydrochloric acid. Instead of hydrochloric acid, nitric acid, acetic acid, or the like may be used. If the pH is higher than 7.0, unreacted calcium may not be completely removed. On the other hand, if the pH is less than 2.5, calcium in the calcium-titanium composite oxide may flow out into the acid, whereby some titanium oxide may form.

(Surface Coating Treatment)

In the present invention, for the purpose of improving a dispersion stability and durability in a dispersion medium when manufacturing, for example, a cosmetic, the pigment composed of particles containing a calcium-titanium composite oxide as a main component may be provided with a coating layer of an inorganic substance like a hydrous oxide or oxide of a metal such as aluminum, silicon, zinc, titanium, zirconium, iron, cerium, or tin on at least a part of the particle surface. A metal salt other than those described above may be used for the inorganic coating. Further, for surface modification exemplified by a hydrophobic treatment, an organic coating layer may be provided at least a part of the particle surface of the pigment of the present invention. Examples of organic coatings include treating with a silicone compound such as dimethylpolysiloxane and methylhydrogenpolysiloxane, a coupling agent such as a silane coupling agent, an aluminum coupling agent, a titanium coupling agent, and a zirconium coupling agent, a fluorine compound such as a perfluoroalkyl phosphate compound, a hydrocarbon, lecithin, an amino acid, polyethylene, a wax, and a metal soap, etc. A plurality of these treatments may be carried out in combination, and the order of the treatments is not particularly limited.

(Uses of Pigment)

The pigment of the present invention can selectively transmit light in a warm color range, and so when used as a material for a cosmetic that is applied to a skin, the transmitted light in the warm color range scatters inside the skin, thereby suppressing white cast and thus enabling a natural finish. Therefore, the pigment of the present invention can be suitably used as a material for a cosmetic. A cosmetic containing the pigment of the present invention is one aspect of the present invention. From another point of view, use of the pigment of the present invention, which consists of particles containing a calcium-titanium composite oxide as a main component, as a cosmetic is also an aspect of the present invention. Further, use of the pigment of the present invention, which consists of particles containing a calcium-titanium composite oxide as a main component, for suppressing a white cast phenomenon in cosmetics can also be said to be an aspect of the present invention. As used herein "the white cast phenomenon" refers to a phenomenon in which the finish of the makeup looks pale and unnatural in the case where the intensity of scattered white light is strong when the cosmetic is applied to a skin. "Suppressing a white cast phenomenon" means that the pigment of the present invention added to the cosmetic selectively transmits light in a warm color range to occur scattering of the transmitted light in the warm color range inside the skin, thereby suppressing, reducing, or alleviating the above-described white cast phenomenon, and thus enabling a more natural makeup finish. As used herein, "light in the warm color range" refers to light with a wavelength of 570 nm or more and 780 nm or less.

The pigment of the present invention can also be used in a wide range of applications in fields other than cosmetics by utilizing its ability to transmit light in the warm color range. Examples of such applications include, but are not limited to, adding to a transparent material and forming a film to use in optical equipment components, adding to a resin to use in sunroofs or the like, and adding to a paint to form coating that transmits light in the warm color range. Further, the pigment obtained by the present invention can also be used as a substitute for titanium oxide.

(Cosmetic)

When using the pigment of the present invention for a cosmetic, typically, the surface thereof may be coated as described above, and then the pigment may be mixed with an inorganic pigment and/or an organic pigment or the like according to a known method. The content of the pigment of the present invention in the cosmetic depends on the type of the cosmetic, and is not particularly limited. For example, for a powder type cosmetic about 1 g/kg or more and 900 g/kg or less of the pigment may be used; for an oily type cosmetic about 1 g/kg or more and 500 g/kg or less of the pigment may be used; and for an emulsion type or a cream type cosmetic about 1 g/kg or more and 150 g/kg or less of the pigment may be used. However, the content is not limited to these ranges.

As the inorganic pigment and/or organic pigment that can be mixed when using the pigment of the present invention as a cosmetic, inorganic pigments, organic pigments, and the like that are used in ordinary cosmetics may be used as necessary. Examples of such inorganic pigments include titanium oxide, zinc oxide, iron oxide represented by red iron oxide, cerium oxide, alumina, zirconium oxide, magnesium oxide, chromium oxide, magnesium silicate, magnesium aluminum silicate, calcium silicate, barium sulfate, magnesium sulfate, calcium sulfate, calcium carbonate, magnesium carbonate, talc, mica, surface-treated mica, a mica-like synthetic pigment, sericite, zeolite, kaolin, bentonite, clay, silicic acid, boron nitride, bismuth oxychloride, hydroxyapatite, ultramarine blue, Prussian blue, and dehydrates and complexes of these. Examples of organic pigments include silicone powder, elastic silicone powder, polyurethane powder, cellulose powder, nylon powder, urethane powder, silk powder, polymethyl methacrylate (hereinafter referred to as "PMMA") powder, polyethylene powder, starch, carbon black, metal soaps such as zinc stearate, and complexes of these. Tar dyes and various natural dyes can also be used.

The method for manufacturing the cosmetic is not particularly limited, and a known method may be used. The form of the cosmetic is also not particularly limited, and may be, for example, a powder, a solid powder, a cream, an emulsion, a lotion, an oily liquid, an oily solid, a paste, or the like. For example, the cosmetic may be a makeup cosmetic such as a makeup base, a foundation, a concealer, a face powder, a control color, a sunscreen cosmetic, a lipstick, a cheek rouge, a lip balm, a lip color, a lip gloss, an eye shadow, an eyeliner, a mascara, a cheek color, a nail polish, a body powder, a perfume powder, and a baby powder, a skin care cosmetic, a hair care cosmetic, and the like. In view of maximizing the light-transmitting effect in the warm color range and the lubricity of the pigment of the present invention, it is preferable to use the pigment of the present invention in a makeup cosmetic to be applied to a skin.

In addition to the above-described ingredients, the cosmetic of the present invention may contain other ingredients depending on the purpose of the cosmetic, as long as they do not impair the effects of the present invention in terms of quantity and quality. For example, oily components, dyes, pH adjusters, moisturizers, thickeners, surfactants, dispersants, stabilizers, colorants, preservatives, antioxidants, sequestering agents, astringents, anti-inflammatory agents, UV absorbers, fragrances, some pharmaceuticals, and the like can be appropriately added depending on the purpose.

The pigment of the present invention can be used in fields other than cosmetics, such as film compositions, resin compositions, paints, and inks. In other words, a film composition, a resin composition, a paint, and an ink containing the pigment of the present invention are each one aspect of the present invention. From another point of view, use of the pigment of the present invention, which consists of particles containing a calcium-titanium composite oxide as a main ingredient, in a film composition, a resin composition, a paint, or an ink is also an aspect of the present invention. Further, for example, use of the pigment of the present invention, which consists of particles containing a calcium-titanium composite oxide as a main ingredient, for manufacturing a film composition, a resin composition, a paint, or an ink that transmits light in the warm color range well can be said to be an aspect of the present invention.

The pigment of the present invention can be used as one of the materials of a film composition. Specific examples of uses of a film composition containing the pigment of the present invention include, but are not limited to, optical equipment, and solar power generation equipment. A film composition is mainly produced from a resin such as polyethylene terephthalate, polypropylene, polyvinyl alcohol, and fluororesin, glass, porous materials, biological materials, and the like. The film composition is produced by a known method. For example, a film composition containing the material of the present invention can be obtained by dissolving a resin in a solvent such as an organic solvent and water, mixing the resultant mixture with the pigment of the present invention that has been dispersed in a solvent in advance, pouring this mixture into a mold, and drying it. Also, dispersants, other pigments, colorants, antistatic agents, and the like can optionally be used. The pigment of the present invention is added such that the amount thereof is in the range of preferably 1 g/kg or more and 250 g/kg or less in the obtained film composition, but the range is not limited to this. By using the pigment of the present invention, it is possible to obtain a film composition that selectively transmits light in the warm color range.

The pigment of the present invention can be used as one of the materials of a resin composition. Specific examples of uses of a resin composition containing the pigment of the present invention include, but are not limited to, sunroofs, containers made of resin, and the like. As the resin, either a thermoplastic resin, such as polyethylene or polypropylene, or a thermosetting resin, such as polycarbonate, may be used. The resin composition is produced by a known method. For example, a resin composition containing the pigment of the present invention can be obtained by dispersing a monomer and the pigment of the present invention in a solvent such as an organic solvent and water, adding a polymerization initiator, heating, washing, and drying. Also, flame retardants, fillers, and the like can optionally be used. The pigment of the present invention is added such that the amount thereof is in the range of preferably 1 g/kg or more and 350 g/kg or less in the obtained resin composition, but the range is not limited to this. By using the pigment of the present invention, it is possible to obtain a resin composition that transmits light in the warm color range, and a white resin composition tinged with warm color.

The pigment of the present invention can be used as one of the materials of a paint. Specific examples of uses of a paint containing the pigment of the present invention include, but are not limited to, a residential paint for cold districts. The pigment of the present invention can be used in both water-based and oil-based paints. The paint can be obtained from a resin such as an acrylic resin, a urethane resin, and polyvinyl alcohol, a solvent such as toluene, ethanol, and water, and a colorant represented by the pigment of the present invention. The paint is produced by a known method. For example, a paint containing the pigment of the present invention can be obtained by adding a curing agent to a resin, then adding the pigment obtained by the present invention and a solvent, and stirring the mixture. Anti-settling agents, preservatives, and other pigments may optionally be used in combination. The pigment of the present invention is added such that the amount thereof is in the range of preferably 1 g/kg or more and 700 g/kg or less in the dried paint film after use, but the range is not limited to this. By using the pigment of the present invention, it is possible to obtain a residential paint that transmits light in the warm color range well, thereby making it easier to raise the indoor temperature.

The pigment of the present invention can be used in an ink. Specific examples of uses of an ink containing the pigment of the present invention include, but are not limited to, a special ink for printing on films, glass surfaces, and the like. The ink can be obtained from a colorant represented by the pigment obtained by the present invention, a resin such as an acrylic resin, and a solvent such as a ketone, a hydrocarbon, and water. The ink is produced by a known method. For example, the ink can be obtained by dispersing and mixing a colorant, a resin, and a solvent. Also, pH adjusters, a surfactant, an antiseptic, and a pigment other than the pigment obtained in the present invention may optionally be used. The pigment of the present invention is added such that the amount thereof is in the range of preferably 1 g/kg or more and 600 g/kg or less in the obtained ink, but the range is not limited to this. By using the pigment of the present invention, it is possible to print on a transparent substrate such as vinyl or glass to give an aesthetic appearance not found in conventional white pigments.

In addition to the above, the pigment of the present invention can be used in applications such as paper, toner external additives, applicators, textile products, packaging materials, films, and coating materials.

Prior to describing the examples, the test methods used in the present invention will be described.

(Lattice Constant a)

Using the X-ray diffractometer RINT-TTR III, manufactured by Rigaku Corporation, X-ray diffractometry was carried out by using a powder method. The sample was ground in a mortar and packed in a cell in an amount of about 1.5 g±0.2 g. The start angle was 5.0000°, the end angle was 90.0000°, the sampling width was 0.0100°, the scan speed was 10.0000°/min, the divergence slit was 0.5°, the scattering slit was 0.5°, and the width of the receiving slit was 0.15 mm. For the characteristic X-rays, copper was used for the cathode and the wavelength was 0.15418 nm. The obtained X-ray diffraction pattern was subjected to smoothing, background processing, and peak detection using analysis software MDI JADE7 by Material Data Inc. to calculate the lattice constant a.

(XRD Diffraction Line Height Ratio and XRD Titanium Oxide Integrated Diffraction Intensity)

The X-ray diffraction pattern measured by the above-described method was subjected to background processing, smoothing, and peak detection using powder X-ray analysis software PDXL2 by Rigaku Corporation. The height of the highest portion of the maximum diffraction line in the range of a diffraction angle 2θ of 32.50° or more and 33.50° or less was defined as 100.0, and the height of the highest portion of the maximum diffraction line in the range of a diffraction angle 2θ of 46.75° or more and 47.75° or less was calculated. The calculation result was used as the XRD diffraction line height ratio. Further, the integrated diffraction intensity of the maximum diffraction line in the range of a diffraction angle 2θ of 32.50° or more and 33.50° or less was defined as 100.0, and the integrated diffraction intensity of maximum diffraction line appearing at a diffraction angle 2θ in the range of 24.75° or more and 28.00° or less was calculated. The calculation result was used as the XRD titanium oxide integrated diffraction intensity.

(Crystallite Size)

The half width of the diffraction line of the (1 2 1) plane obtained from the X-ray diffraction pattern measured by the above method was substituted into the following Sherrer equation to calculate the crystallite size $D_{121}$:

$$D_{121} = k\lambda / \beta \cos \theta$$

where the constant k is 0.9, λ is the X-ray wavelength, β is the half width of the diffraction line on the (1 2 1) plane, and cos θ is based on the diffraction angle 2θ at which the diffraction line appears.

(Specific Surface Area)

The specific surface area was measured by a BET single-point method using a Gemini VII2390 manufactured by MICROMETORITICS.

(Particle Size Distribution)

The particle size distribution was measured by a method according to JIS Z 8825:2013 using a laser beam diffraction scattering particle size analyzer, Microtrac (registered trademark) MT3300EX II, manufactured by MicrotracBEL Corp. Deionized water was used as the dispersion medium. An appropriate amount of the pigment was added dropwise into an ultrasonic dispersing tank of an automatic sample circulator attached to the analyzer, and then ultrasonication for dispersing was performed at an output of 40 W for 360 seconds. After that, as the various measurement parameters, the refractive index of the deionized water was set to 1.33, the light transmittance of the particles to be measured was set to "reflect", and the measurement time was set to 30 seconds. The particle size (X10) corresponding to 10% of the cumulative particle size distribution (by volume) and the particle size (X90) corresponding to 90% of the cumulative particle size distribution (by volume) were measured, and X90/X10 was used as an index of the particle size distribution.

(Degree of circularity and average circularity)

The degree of circularity was calculated by $(4\pi \times S)/L^2$, where S is the area of the particle when projected in two dimensions, and L is the observed perimeter of the particle. Using a transmission electron microscope JEM-1400plus manufactured by JEOL Ltd., the particles were photographed at an observation magnification of 10,000×, and the degree of circularity was calculated using image analysis software ImageJ. The average circularity was the average value of the degree of circularity of 200 particles.

(Warm Color Light-Transmitting Effect)

3 mL of a styrenated alkyd resin and 0.5 g of pigment were kneaded to form a paint using an H3-type Automatic Hoover Muller manufactured by Toyo Seiki Seisaku-sho, Ltd., and the resulting dispersion was applied to a black-and-white test paper for the concealment rate test, JIS-K5 400, with a 3 mil doctor blade and baked at 130° C. for 30 minutes to obtain a test sample. On the test sample on the black background, the reflection rates in a wavelength in the range of 380 nm or more and 780 nm or less were measured using a spectral color difference meter SQ-2000 manufactured by Nippon Denshoku Industries Co., Ltd. The transmittance at each wavelength was calculated by subtracting the obtained reflection rates from 100%. The sum of the transmittances in a wavelength in the range of 380 nm or more and 780 nm or less was taken as the total amount of transmitted light, the sum of the transmittances in a wavelength in the range of 570 nm or more and 780 nm or less was taken as the amount of warm color transmission light, and the value of the amount of warm color transmission light/the total amount of transmission light was taken as the warm color light-transmitting effect.

EXAMPLES

The present invention will be specifically described below by way of examples, but the following examples are merely for illustrative purposes, and the scope of the invention is not limited by these.

In the stirring operation in the examples and comparative examples, taking properties related to the behavior of the liquid during stirring, such as the amount of liquid, the viscosity of the liquid, and the shape of the container, into consideration, the rotation speed for stirring was adjusted appropriately so that the entire liquid was uniformly mixed and that droplets are not scattered around. For chemicals such as sodium hydroxide, the company name of the manufacturer and distributor thereof will be omitted, in the case where the same effect can be obtained by using any company's product as long as it is a general commercially available product.

Example 1

Metatitanic acid obtained by a sulfuric acid method was subjected to a deironizing and bleaching treatment, and then an aqueous solution of sodium hydroxide was added to adjust the pH to 9.0 to carry out desulfurization. Then, hydrochloric acid was added until the pH reached 5.8 to carry out nueutralization. The resultant solution was filtered, and the filter cake was washed to obtain a metatitanic acid cake having a sulfur content of 9.3 g/kg in terms of $SO_3$. Water was added to the washed cake to prepare a slurry of 2.13 mol/L in terms of Ti, then hydrochloric acid was added to adjust the pH to 1.4, and then a deflocculation treatment was carried out. The slurry after the treatment in an amount of 2.25 mol in terms of $TiO_2$ was collected and placed in a reaction vessel with a capacity of 3000 mL. Calcium hydroxide was added thereto such that the mole of calcium, Ca, was 1.15 times the mole of titanium, Ti. 0.36 mol of sodium hydroxide was added thereto, and water was added such that the total volume became 2.0 L. The mixed solution was stirred for 30 minutes using HEIDON600G manufactured by Shinto Scientific Co., Ltd.

The slurry was heated to 95° C. using a B-E type mantle heater manufactured by Tokyo Technological Labo co., LTD. while further stirring and mixing the slurry. Stirring was continued for 18 hours to complete the reaction (normal pressure heating reaction). The stirred slurry was allowed to cool to 50° C., hydrochloric acid was added until the pH reached 5.0, and stirring was continued for additional one hour (calcium removal treatment). The resulting precipitate was washed by decantation, separated by filtration, and dried in air at 120° C. for 10 hours using a Perfect Oven PHH-202 manufactured by ESPEC. CORP. The dried product was pulverized with an Ishikawa stirring and crushing machine AGA model manufactured by Ishikawa Kojo Co., Ltd. (hereinafter referred to as "automatic mortar") to obtain a white pigment. The pigment was evaluated by the test methods described above, and the results were as follows: the lattice constant a was 5.4924 Å, the XRD diffraction line height ratio was 37.3, the specific surface area was 12.2 $m^2/g$, and the XRD titanium oxide integrated diffraction intensity was 6.07. The particles had a rectangular parallelepiped shape, the crystallite size was 389 Å, the particle size distribution was 2.81, and the average circularity was 0.720. The warm color light-transmitting effect was 0.64.

Example 2

A white pigment was obtained by performing the normal pressure heating reaction, calcium removal treatment, washing, filtration, drying, and pulverization in the same manner as in Example 1, except that the amount of sodium hydroxide added after the addition of calcium hydroxide was changed to 1.80 mol. The pigment had a lattice constant a of 5.5022 Å, an XRD diffraction line height ratio of 38.3, a specific surface area of 6.1 $m^2/g$, and an XRD titanium oxide integrated diffraction intensity of 5.85. The particles had a rectangular parallelepiped shape. The crystallite size was 420 Å, the particle size distribution was 2.92, and the average circularity was 0.698. The warm color light-transmitting effect was 0.58.

Example 3

A white pigment was obtained by performing the normal pressure heating reaction, calcium removal treatment, washing, filtration, drying, and pulverization in the same manner as in Example 1, except that the amount of sodium hydroxide added after the addition of calcium hydroxide was changed to 7.20 mol. The pigment had a lattice constant a of 5.4924 Å, an XRD diffraction line height ratio of 37.8, a specific surface area of 4.4 $m^2/g$, and an XRD titanium oxide integrated diffraction intensity of 4.24. The particles had a rectangular parallelepiped shape. The crystallite size was 377 Å, the particle size distribution was 4.26, and the average circularity was 0.692. The warm color light-transmitting effect was 0.56.

Example 4

A white pigment was obtained by performing the normal pressure heating reaction, calcium removal treatment, washing, filtration, drying, and pulverization in the same manner as in Example 1, except that the amount of sodium hydroxide added after the addition of calcium hydroxide was changed to 3.60 mol, and that 0.0193 mol of glucose was added per 1 mol of Ca after the addition of sodium hydroxide. The pigment had a lattice constant a of 5.4809 Å, an XRD diffraction line height ratio of 33.2, a specific surface area of 27.4 $m^2/g$, and an XRD titanium oxide integrated diffraction intensity of 3.14. The particles had an approximately spherical shape. The crystallite size was 339 Å, the particle size distribution was 2.71, and the average circularity was 0.835. The warm color light-transmitting effect was 0.63.

Example 5

A white pigment was obtained by performing the normal pressure heating reaction, calcium removal treatment, washing, filtration, drying, and pulverization in the same manner as in Example 4, except that the amount of glucose added per 1 mol of Ca was changed to 0.0077 mol. The pigment had a lattice constant a of 5.4907 Å, an XRD diffraction line height ratio of 38.0, a specific surface area of 5.5 $m^2/g$, and an XRD titanium oxide integrated diffraction intensity of 5.31. The particles had a rectangular parallelepiped shape. The crystallite size was 533 Å, the particle size distribution was 3.02, and the average circularity was 0.740. The warm color light-transmitting effect was 0.59.

Example 6

A white pigment was obtained by performing the normal pressure heating reaction, calcium removal treatment, washing, filtration, drying, and pulverization in the same manner as in Example 5, except that 0.0166 mol of citric acid per 1 mol of Ca was added after the addition of glucose. The pigment had a lattice constant a of 5.4907 Å, an XRD diffraction line height ratio of 40.9, a specific surface area of 8.0 $m^2/g$, and an XRD titanium oxide integrated diffraction intensity of 8.42. The particles had a rectangular parallelepiped shape. The crystallite size was 539 Å, the particle size distribution was 2.67, and the average circularity was 0.614. The warm color light-transmitting effect was 0.58.

Example 7

A white pigment was obtained by performing the normal pressure heating reaction, calcium removal treatment, washing, filtration, drying, and pulverization in the same manner as in Example 4, except that the amount of glucose added per 1 mol of Ca was changed to 0.0039 mol. The pigment had a lattice constant a of 5.5007 Å, an XRD diffraction line height ratio of 45.7, a specific surface area of 3.6 $m^2/g$, and an XRD titanium oxide integrated diffraction intensity of 5.22. The particles had a rectangular parallelepiped shape. The crystallite size was 277 Å, the particle size distribution was 3.51, and the average circularity was 0.699. The warm color light-transmitting effect was 0.56.

Example 8

A white pigment was obtained in the same manner as in Example 1, except for the following: the amount of slurry collected after the deflocculation treatment was changed to 1.50 mol as $TiO_2$, the amount of sodium hydroxide added was changed to 0.60 mol, the holding time at 95° C. was changed to 4 hours, and the drying temperature and the drying time after separation by filtration were changed to 60° C. and 2 hours, respectively. The pigment had a lattice constant a of 5.5021 Å, an XRD diffraction line height ratio of 41.5, a specific surface area of 9.4 $m^2/g$, and an XRD titanium oxide integrated diffraction intensity of 5.33. The particles had a rectangular parallelepiped shape. The crystallite size was 355 Å, the particle size distribution was 2.44, and the average circularity was 0.689. The warm color light-transmitting effect was 0.59.

Example 9

A white pigment was obtained by drying the pigment obtained in Example 8 and then firing it in air at 300° C. using a Super-C C-2035D manufactured by MOTOYAMA CO., LTD. (hereinafter referred to as "firing furnace"). The pigment had a lattice constant a of 5.4759 Å, an XRD diffraction line height ratio of 41.7, a specific surface area of 8.2 m$^2$/g, and an XRD titanium oxide integrated diffraction intensity of 4.85. The particles had a rectangular parallelepiped shape. The crystallite size was 423 Å, the particle size distribution was 2.52, and the average circularity was 0.655. The warm color light-transmitting effect was 0.59.

Comparative Example 1

A pigment composed mainly of a calcium-titanium composite oxide was synthesized by a general firing method. Specifically, metatitanic acid that was the deflocculation-treated product described in Example 1, and calcium carbonate were added such that the mole of calcium, Ca, was 1.15 times the mole of titanium, Ti, and they were rehydrated such that the solid content became 200 g/L. The pH was adjusted to 10.0 with sodium hydroxide. The resultant was then dispersed and mixed using an Ultra Apex Mill UAM-015 (hereinafter referred to as "bead mill") manufactured by Hiroshima Metal & Machinery Co., Ltd. The solids were separated from the slurry by filtration, and dried in air at 120° C. for 10 hours. The dried product was fired in air at 1100° C. for 1 hour in a firing furnace, and the fired product was then pulverized with an automatic mortar to obtain a pale pink pigment. The pigment had a lattice constant a of 5.4465 Å, an XRD diffraction line height ratio of 54.0, a specific surface area of 4.7 m$^2$/g, and an XRD titanium oxide integrated diffraction intensity of 2.63. The particles had an approximately spherical shape, because each particle was melted partially and fused with each other by firing at high temperatures. The crystallite size was 383 Å, the particle size distribution was 19.92, and the average circularity was 0.818. The warm color light-transmitting effect was 0.51.

Comparative Example 2

A pale ocher pigment was obtained by firing the pigment obtained in Example 1 in a firing furnace at 1100° C. for 1 hour and then pulverizing with an automatic mortar. The pigment had a lattice constant a of 5.4436 Å, an XRD diffraction line height ratio of 53.2, a specific surface area of 6.7 m$^2$/g, and an XRD titanium oxide integrated diffraction intensity of 2.55. The particles had an approximately spherical shape. The crystallite size was 373 Å, the particle size distribution was 63.54, and the average circularity was 0.838. The warm color light-transmitting effect was 0.53.

Comparative Example 3

A pale ocher pigment was obtained by firing the pigment obtained in Example 4 in a firing furnace at 1100° C. for 1 hour and then pulverizing with an automatic mortar. The pigment had a lattice constant a of 5.4514 Å, an XRD diffraction line height ratio of 52.2, a specific surface area of 5.4 m$^2$/g, and an XRD titanium oxide integrated diffraction intensity of 2.05. The particles had an approximately spherical shape. The crystallite size was 415 Å, the particle size distribution was 100.82, and the average circularity was 0.822. The warm color light-transmitting effect was 0.55.

Comparative Example 4

A commercially available calcium-titanium composite oxide reagent CAF04PB manufactured by Kojundo Chemical Lab. Co., Ltd. was used as the pigment of Comparative Example 4. The appearance of the reagent was light pink. The pigment had a lattice constant a of 5.4420 Å, an XRD diffraction line height ratio of 52.3, a specific surface area of 2.5 m$^2$/g, and an XRD titanium oxide integrated diffraction intensity of 3.72. The particles had an approximately spherical shape. The crystallite size was 556 Å, the particle size distribution was 13.19, and the average circularity was 0.791. The warm color light-transmitting effect was 0.53.

Table 1 shows the manufacturing conditions of the pigments of the examples and comparative examples, and Table 2 shows the properties of the pigments obtained in the examples and comparative examples.

As shown in Table 2, the pigments of Examples 1 to 9, which had a lattice constant a of 5.4700 Å or more and 5.5100 Å or less, can be said to be pigments that have a warm color light-transmitting effect of 0.56 or more and that selectively transmit light in a warm color range. On the other hand, the pigments of Comparative Examples 1 to 4, which had a lattice constant a that was smaller than 5.4700 Å, had a warm color light-transmitting effect as small as 0.55 or less.

As described above, the pigment of the present invention can selectively transmit light in the warm color range. The pigment of the present invention can achieve a natural finish when used as an ingredient for cosmetics.

TABLE 1

|  | Amount of deflocculated slurry collected [1] mol | Amount of calcium added with respect to titanium mol/mol | Amount of sodium hydroxide added mol/L | Amount of glucose added [2] mol/mol | Amount of citric acid added [3] mol/mol | Holding time of heating and stirring h | Drying temperature ° C. | Drying time h | Firing temperature ° C. | Firing time h |
|---|---|---|---|---|---|---|---|---|---|---|
| Example 1 | 2.25 | 1.15 | 0.18 | 0.0000 | 0.0000 | 18 | 120 | 10 | — | — |
| Example 2 | 2.25 | 1.15 | 0.90 | 0.0000 | 0.0000 | 18 | 120 | 10 | — | — |
| Example 3 | 2.25 | 1.15 | 3.60 | 0.0000 | 0.0000 | 18 | 120 | 10 | — | — |
| Example 4 | 2.25 | 1.15 | 1.80 | 0.0193 | 0.0000 | 18 | 120 | 10 | — | — |
| Example 5 | 2.25 | 1.15 | 1.80 | 0.0077 | 0.0000 | 18 | 120 | 10 | — | — |

TABLE 1-continued

|  | Amount of deflocculated slurry collected [1] mol | Amount of calcium added with respect to titanium mol/mol | Amount of sodium hydroxide added mol/L | Amount of glucose added [2] mol/mol | Amount of citric acid added [3] mol/mol | Holding time of heating and stirring h | Drying temperature °C. | Drying time h | Firing temperature °C. | Firing time h |
|---|---|---|---|---|---|---|---|---|---|---|
| Example 6 | 2.25 | 1.15 | 1.80 | 0.0077 | 0.0166 | 18 | 120 | 10 | — | — |
| Example 7 | 2.25 | 1.15 | 1.80 | 0.0039 | 0.0000 | 18 | 120 | 10 | — | — |
| Example 8 | 1.50 | 1.15 | 0.30 | 0.0000 | 0.0000 | 4 | 60 | 2 | — | — |
| Example 9 | 1.50 | 1.15 | 0.30 | 0.0000 | 0.0000 | 4 | 60 | 2 | 300 | 1 |
| Comparative Example 1 [4] | — | 1.15 | — | — | — | — | 120 | 10 | 1100 | 1 |
| Comparative Example 2 | 2.25 | 1.15 | 0.18 | 0.0000 | 0.0000 | 18 | 120 | 10 | 1100 | 1 |
| Comparative Example 3 | 2.25 | 1.15 | 1.80 | 0.0193 | 0.0000 | 18 | 120 | 10 | 1100 | 1 |
| Comparative Example 4 [5] | — | — | — | — | — | — | — | — | — | — |

[1] Amount calculated in terms of $TiO_2$.
[2] Mole of glucose with respect to mole of calcium added during normal pressure heating reaction.
[3] Mole of citric acid with respect to mole of calcium added during normal pressure heating reaction.
[4] Sample obtained by mixing metatitanic acid and calcium carbonate and then firing.
[5] Commercially-available produce was purchased, and thus the production conditions are not known.

TABLE 2

|  | Lattice constant a Å | XRD diffraction line height ratio | Specific surface area m²/g | XRD titanium oxide integrated diffraction intensity | Particle shape | Crystallite size Å | Particle size distribution | Average circularity | Warm color light-transmitting effect |
|---|---|---|---|---|---|---|---|---|---|
| Example 1 | 5.4924 | 37.3 | 12.2 | 6.07 | rectangular parallelepiped shape | 389 | 2.81 | 0.720 | 0.64 |
| Example 2 | 5.5022 | 38.3 | 6.1 | 5.85 | rectangular parallelepiped shape | 420 | 2.92 | 0.698 | 0.58 |
| Example 3 | 5.4924 | 37.8 | 4.4 | 4.24 | rectangular parallelepiped shape | 377 | 4.26 | 0.692 | 0.56 |
| Example 4 | 5.4809 | 33.2 | 27.4 | 3.14 | approximately spherical shape | 339 | 2.71 | 0.835 | 0.63 |
| Example 5 | 5.4907 | 38.0 | 5.5 | 5.31 | rectangular parallelepiped shape | 533 | 3.02 | 0.740 | 0.59 |
| Example 6 | 5.4907 | 40.9 | 8.0 | 8.42 | rectangular parallelepiped shape | 539 | 2.67 | 0.614 | 0.58 |
| Example 7 | 5.5007 | 45.7 | 3.6 | 5.22 | rectangular parallelepiped shape | 277 | 3.51 | 0.699 | 0.56 |
| Example 8 | 5.5021 | 41.5 | 9.4 | 5.38 | rectangular parallelepiped shape | 355 | 3.44 | 0.689 | 0.59 |
| Example 9 | 5.4759 | 41.7 | 8.2 | 4.85 | rectangular parallelepiped shape | 423 | 2.52 | 0.655 | 0.59 |
| Comparative Example 1 | 5.4465 | 54.0 | 4.7 | 2.63 | approximately spherical shape | 383 | 19.92 | 0.818 | 0.51 |
| Comparative Example 2 | 5.4436 | 53.2 | 6.7 | 2.55 | approximately spherical shape | 373 | 63.54 | 0.838 | 0.53 |
| Comparative Example 3 | 5.4514 | 52.2 | 5.4 | 3.05 | approximately spherical shape | 415 | 100.82 | 0.822 | 0.55 |
| Comparative Example 4 | 5.4420 | 52.3 | 3.5 | 3.72 | approximately spherical shape | 556 | 13.19 | 0.791 | 0.53 |

Next, powder foundations produced by using the pigments obtained in the examples and comparative examples were subjected to a sensory evaluation by the following method.

(Sensory Evaluation of Powder Foundation)

Each pigment obtained in the examples and comparative examples was subjected to a surface treatment with methylhydrogenpolysiloxane, and the ingredients were uniformly mixed according to the formulation shown in Table 3 using a LAB. Mixer LM-110T manufactured by HANIL Electric. Co., Lid (hereinafter referred to as "mixer"). The mixture was pulverized using a sample mill TASM-1 manufactured by Tokyo Atomizer M.F.G. Co., Ltd. (hereinafter referred to as "sample mill"). A predetermined amount of the resultant was then filled in a metal plate and compression molded to produce a powder foundation.

TABLE 3

| Ingredient | Amount added (g/kg) |
|---|---|
| Pigment obtained from example or comparative example after surface treatment with methylhydrogenpolysiloxane | 100.0 |
| Mica | 300.0 |
| Talc | 481.2 |
| Coloring pigment | 18.8 |
| Squalane | 100.0 |

Ten panelists applied each of the obtained powder foundations on their arms and faces, especially on areas with dullness, spots, and the like, until the dullness, spots, or the like became inconspicuous, and the natural finish and lubricity were evaluated.
(Natural Finish)
The impression from a visual comparison with areas where foundation was not applied was evaluated according to the following criteria, and whether or not a "natural finish" was achieved was determined based on the average score of the 10 panelists. A higher score means that the foundation had less "white cast" and achieved a "natural finish".
Table 4 shows the results of the sensory evaluation.
(Evaluation Criteria)
  5 points: Indistinguishable from non-applied areas even when viewed at close range.
  4 points: Indistinguishable from non-applied areas when viewed from a position 1 m away.
  3 points: No sense of incongruity when viewed from a position 1 m away.
  2 points: White when viewed from a close distance.
  1 point: White enough to be recognized even from a distant position.
(Criteria)
  In the range of 4.0 points or more and 5.0 points or less: A
  In the range of 3.0 points or more and less than 4.0 points: B
  In the range of 2.0 points or more and less than 3.0 points: C
  In the range of 1.0 points or more and less than 2.0 points: D
(Lubricity)
The feel of the foundation when spread with fingers was evaluated according to the following criteria, and the "lubricity" was determined by the average score of the 10 panelists. The higher the score, the better the lubricity of the foundation. Table 4 shows the results of the sensory evaluation.

Evaluation Criteria 5 points: It is possible to be spread thinly by sliding on the skin.
  4 points: It is possible to be spread smoothly over a wide area.
  3 points: It is possible to be spread without unpleasantness.
  2 points: It is impossible to be spread well.
  1 point: Roughness is felt when spread on the skin.

Criteria

In the range of 4.0 points or more and 5.0 points or less: A
  In the range of 3.0 points or more and less than 4.0 points: B
  In the range of 2.0 points or more and less than 3.0 points: C
  In the range of 1.0 points or more and less than 2.0 points: D

TABLE 4

| Sensory test item | Natural finish | Lubricity |
|---|---|---|
| Example 1 | A | B |
| Example 2 | B | B |
| Example 3 | B | B |
| Example 4 | A | A |
| Example 5 | B | A |
| Example 6 | B | B |
| Example 7 | B | B |
| Example 8 | B | B |
| Example 9 | B | B |
| Comparative Example 1 | C | C |
| Comparative Example 2 | C | D |
| Comparative Example 3 | C | D |
| Comparative Example 4 | C | C |

As a result of the sensory evaluation, the foundations produced by using the pigment of the present invention all provided a finish that looked like the natural bare skin and had better lubricity, compared to the foundations containing the pigments of the comparative examples. Thus, when the pigment of the present invention is incorporated into a cosmetic, the cosmetic provided can produce a finish that looks like the natural bare skin and exhibit excellent lubricity.

Example 10

(Manufacture of Powder Foundation)
The ingredients 1 to 13 below were mixed and uniformly pulverized (step A). Then, ingredients 15 to 17 were uniformly mixed and added to the pulverized mixture obtained in step A to obtain a uniform mixture (step B). Ingredient 14 was then added thereto, and the resulting mixture was press-molded in a mold to obtain a powder foundation (step C).

It was confirmed that the obtained powder foundation did not cause white cast when applied to a skin, provided a finish that looked like a natural bare skin, and had good lubricity.

| (Ingredients) | compound ratio (g/kg) |
|---|---|
| 1. Caprylyl silane-treated mica (Note 1) | 400 |
| 2. Caprylyl silane-treated pigment described in Example 6 (Note 1) | 50 |
| 3. Silicone-treated talc (Note 2) | balance |
| 4. Silicone-treated, pigment-grade titanium oxide (Note 2) | 50 |
| 5. Silicone-treated titanium dioxide fine particle (Note 2) | 50 |
| 6. Silicone-treated barium sulfate (Note 2) | 100 |
| 7. Silicone-treated red iron oxide (Note 2) | 4 |

-continued

| (Ingredients) | compound ratio (g/kg) |
|---|---|
| 8. Silicone-treated yellow iron oxide (Note 2) | 20 |
| 9. Silicone treated amber (Note 2) | 4 |
| 10. Silicone-treated black iron oxide (Note 2) | 1 |
| 11. Phenyl-modified hybrid silicone composite powder (Note 3) | 20 |
| 12. Spherical polymethylsilsesquioxane powder (Note 4) | 5 |
| 13. Preservative | appropriate amount |
| 14. Fragrance | appropriate amount |
| 15. Crosslinked dimethylpolysiloxane (Note 5) | 40 |
| 16. Glyceryl trioctanoate | 20 |
| 17. Squalane | 10 |

(Note 1)
Surface treated with AES-3083 manufactured by Shin-Etsu Chemical Co., Ltd.
(Note 2)
Surface treated with KF-9909 manufactured by Shin-Etsu Chemical Co., Ltd.
(Note 3)
KSP-300 manufactured by Shin-Etsu Chemical Co., Ltd.
(Note 4)
KMP-590 manufactured by Shin-Etsu Chemical Co., Ltd.
(Note 5)
KSG-16 manufactured by Shin-Etsu Chemical Co., Ltd.

Example 11

(Manufacture of Pressed Powder)

The ingredients 1 to 7 below were mixed and pulverized (step A). The mixed pulverized product was then transferred to a mixer, ingredients 8 to 12 were added, and they were stirred and mixed so as to become uniform (step B). The mixture was then pulverized using a sample mill, and the resultant was press-molded in an aluminum plate to obtain a pressed powder (step C). It was confirmed that the obtained pressed powder did not cause white cast when applied to the skin, provided a finish that looked like the natural bare skin feel, and had good lubricity.

| (Ingredients) | compound ratio (g/kg) |
|---|---|
| 1. Talc | balance |
| 2. PMMA (Note 1) | 100 |
| 3. Sericite | 300 |
| 4. Scaly silica (Note 2) | 30 |
| 5. Pigment described in Example 7 | 60 |
| 6. Preservative | appropriate amount |
| 7. Color material | appropriate amount |
| 8. Octyl methoxycinnamate | 30 |
| 9. Squalane | 20 |
| 10. Preservative | appropriate amount |
| 11. Antioxidant | appropriate amount |
| 12. Fragrance | appropriate amount |

(Note 1)
Matsumoto Microsphere M-100, 7 μm product, manufactured by Matsumoto Yushi-Seiyaku Co., Ltd.
(Note 2)
Sunlovely C manufactured by Dokai Chemical Industry Co., Ltd.

Example 12

(Manufacture of Loose Powder)

The ingredients 1 to 7 below were mixed and pulverized (step A). The mixed pulverized product was then transferred to a mixer, ingredients 8 to 10 were added, and they were stirred and mixed so as to become uniform (step B). The mixture obtained in step B was further pulverized using a sample mill and packed to obtain a loose powder (step C).

It was confirmed that the obtained loose powder did not cause white cast when applied to the skin, provided a finish that looked like the natural bare skin, and had good lubricity.

| (Ingredients) | compound ratio (g/kg) |
|---|---|
| 1. Talc | balance |
| 2. Pigment described in Example 7 | 10 |
| 3. Amihope LL | 30 |
| 4. PMMA (Note 1) | 80 |
| 5. Preservative | appropriate amount |
| 6. Color material | appropriate amount |
| 7. Squalane | 10 |
| 8. Preservative | appropriate amount |
| 9. Antioxidant | appropriate amount |
| 10. Fragrance | appropriate amount |

(Note 1)
Matsumoto Microsphere S-100, 10 μm product, manufactured by Matsumoto Yushi-Seiyaku Co., Ltd.

Example 13

(Manufacture of Oily Foundation)

The ingredients 1 to 6 below were mixed in a mixer and pulverized uniformly (step A). Then, ingredients 7 to 16 were heated to 85° C. to dissolve, the mixed pulverized product obtained in step A was added thereto, and the resultant was stirred uniformly (step B). The mixture was defoamed, and then the solids were poured into a tray and slowly cooled to room temperature to obtain an oily foundation (step C).

It was confirmed that the obtained oily foundation did not cause white cast when applied to the skin, provides a finish that looked like the natural bare skin, and had good lubricity.

| (Ingredients) | compound ratio (g/kg) |
|---|---|
| 1. Silicone-treated talc (Note 1) | 53 |
| 2. Silicone treated pigment described in Example 4 (Note 1) | 150 |
| 3. Silicone-treated sericite (Note 1) | 282 |
| 4. Silicone-treated red iron oxide (Note 1) | 5 |
| 5. Silicone treated yellow iron oxide (Note 1) | 18 |
| 6. Silicone-treated black iron oxide (Note 1) | 2 |
| 7. Candelilla wax | 10 |
| 8. Carnauba wax | 10 |
| 9. Ceresin | 15 |
| 10. Decamethylcyclopentasiloxane | 140 |
| 11. Isononyl isononanoate | balance |
| 12. Polyglyceryl diisostearate | 20 |
| 13. Dextrin palmitate | 10 |
| 14. Octyl methoxycinnamate | 30 |
| 15. Preservative | appropriate amount |
| 16. Antioxidant | appropriate amount |

(Note 1)
Surface treated with KF-96A-50cs manufactured by Shin-Etsu Chemical Co., Ltd.

Example 14

(Manufacture of Stick Foundation)

The ingredients 12 to 16 below were mixed in a mixer (step A). Further, ingredients 1 to 11 were weighed into a container capable of holding the entire amount, and heated to 85° C. to dissolve (step B). In addition, ingredients 17 to 21 were weighed into a separate container and dissolved (step C). Then, the mixture obtained in step A was added to the thermally-dissolved mixture obtained in step B and dispersed therein using a stirrer until the resulting mixture became visually uniform, and the thermally-dissolved mixture obtained in step C was further added thereto to emulsify (step D). The mixture was defoamed, and the solids were then poured into a mold and slowly cooled to room temperature to obtain a stick foundation (step E).

It was confirmed that the obtained stick foundation did not cause white cast when applied to the skin, provided a finish that looked like the natural bare skin, and had good lubricity

| (Ingredients) | compound ratio (g/kg) |
|---|---|
| 1. Dimethyl polysiloxane | 180 |
| 2. Decamethylcyclopentasiloxane | 300 |
| 3. Octyl methoxycinnamate | 50 |
| 4. Diisostearyl malate | 40 |
| 5. Candelilla wax | 60 |
| 6. Hydrogenated jojoba ester | 40 |
| 7. Cetyl dimethicone copolyol | 20 |
| 8. Sorbitan sesquiisostearate | 5 |
| 9. Antioxidant | appropriate amount |
| 10. Preservative | appropriate amount |
| 11. Fragrance | appropriate amount |
| 12. Silicone-treated coloring agent (Note 1) | 5 |
| 13. Silicone-treated pigment described in Example 1 (Note 1) | 85 |
| 14. Silicone-treated talc (Note 1) | 60 |
| 15. Silicone-treated mica (Note 1) | 20 |
| 16. Polymethyl methacrylate | 20 |
| 17. Purified water | balance |
| 18. Sodium citrate | 3 |
| 19. 1,3-Butylene glycol | 30 |
| 20. Glycerin | 20 |
| 21. Preservative | appropriate amount |

(Note 1)
Surface treated with KF-99P manufactured by Shin-Etsu Chemical Co., Ltd.

Example 15

(Manufacture of W/O Emulsified Foundation)

The ingredients 12 to 14 below were stirred and mixed using a mixer (step A), and then ingredients 1 to 11 were added and dispersed therein using a stirrer until the resulting mixture became visually uniform (step B). Ingredients 15 to 19 were heated and dissolved in a separate container (step C). Then, the thermally-dissolved mixture obtained in step C was added to the dispersion obtained in step B to emulsify, and then cooled to room temperature to obtain a W/O emulsified foundation (step D).

It was confirmed that the obtained W/O emulsified foundation did not cause white cast when applied to the skin, provided a finish that looked like the natural bare skin, and had good lubricity.

| (Ingredients) | compound ratio (g/kg) |
|---|---|
| 1. POE modified silicone (Note 1) | 8 |
| 2. Polyglyceryl polyricinoleate | 5 |
| 3. Neopentyl glycol dicaprate | 30 |
| 4. Squalane | 10 |
| 5. Pentaerythrityl tetraoctanoate | 20 |
| 6. Inulin stearate (Note 2) | 10 |
| 7. Octyl methoxycinnamate | 40 |
| 8. Decamethylcyclopentasiloxane | 154 |
| 9. Preservative | appropriate amount |
| 10. Antioxidant | appropriate amount |
| 11. Fragrance | appropriate amount |
| 12. Silicone-treated pigment described in Example 5 (Note 3) | 80 |
| 13. Silicone-treated talc (Note 3) | 57 |
| 14. Silicone-treated coloring agent (Note 3) | 10 |
| 15. Purified water | balance |
| 16. 1,3-Butylene glycol | 60 |
| 17. Glycerin | 10 |
| 18. Sodium chloride | 10 |
| 19. Preservative | appropriate amount |

(Note 1)
Product with an HLB value of 4.5
(Note 2)
Rheopearl (registered trademark) ISK manufactured by Chiba Flour Milling Co., Ltd.
(Note 3)
Surface treated with KF-9901 manufactured by Shin-Etsu Chemical Co., Ltd.

Example 16

(Manufacture of O/W Emulsified Foundation)

Ingredients 1 to 7 were heated at 85° C. to dissolve (step A). Separately, ingredients 8 to 10 were mixed and pulverized (step B). Further separately, ingredients 11 to 15 were heated to 85° C. to obtain a dissolved mixture (step C). Then, the pulverized mixture obtained in step B was added to the thermally-dissolved mixture obtained in step A, and dispersed therein using a stirrer until the resulting mixture became visually uniform. The thermally-dissolved mixture obtained in step C was gradually added thereto to emulsify, and the emulsified mixture was cooled to room temperature while stirring. Next, the cooled mixture was filled into an appropriate container to obtain an O/W emulsified foundation (step D).

It was confirmed that the O/W emulsified foundation did not cause white cast when applied to the skin, provided a finish that looked like the natural bare skin, and had good lubricity.

| (Ingredients) | compound ratio (g/kg) |
|---|---|
| 1. Stearic acid | 4 |
| 2. Isostearic acid | 3 |
| 3. Cetyl 2-ethylhexanoate | 40 |
| 4. Liquid paraffin | 110 |
| 5. Polyoxyethylene (10) stearyl ether | 20 |
| 6. Cetyl alcohol | 3 |
| 7. Preservative | 2 |
| 8. Talc | 150 |
| 9. Coloring agent | 40 |
| 10. Pigment described in Example 1 | 30 |
| 11. Triethanolamine | 4 |
| 12. Propylene glycol | 50 |
| 13. Purified water | 541 |
| 14. Preservative | 2 |
| 15. Antioxidant | 1 |

Example 17

(Manufacture of W/O Liquid Foundation)

The ingredients 8 to 12 below were uniformly mixed (step A). Then, a part of ingredient 4 and ingredient 13 were mixed, and the resultant was added to the mixture obtained in step A, and dispersed therein using a stirrer until the resulting mixture became visually uniform (step B). Separately, ingredients 1 to 3, the rest of ingredient 4, and ingredients 5 to 7 were mixed and dispersed using a stirrer until the resulting mixture became visually uniform (step C). Further separately, ingredients 14 to 18 and ingredient 20 were mixed and dispersed using a stirrer until the resulting mixture became visually uniform (step D). The mixture obtained in step D was gradually added under stirring to the mixture obtained in step C to emulsify, and the dispersion obtained in step B and ingredient 19 were further added thereto to obtain a W/O liquid foundation (step E).

It was confirmed that the obtained W/O liquid foundation did not cause white cast when applied to the skin, provided a finish that looked like the natural bare skin, and had good lubricity.

| (Ingredients) | compound ratio (g/kg) |
|---|---|
| 1. Crosslinked polyether-modified silicone (Note 1) | 30 |
| 2. Crosslinked dimethylpolysiloxane (Note 2) | 50 |
| 3. Branched polyether-modified silicone (Note 3) | 20 |
| 4. Decamethylcyclopentasiloxane | 211 |
| 5. Cetyl isooctanoate | 50 |
| 6. Dimethylpolysiloxane (Note 4) | 65 |
| 7. Dimethyl distearyl ammonium hectorite | 12 |
| 8. Silicone-treated pigment described in Example 1 (Note 5) | 50 |
| 9. Silicone-treated pigment-grade titanium oxide (Note 5) | 50 |
| 10. Silicone-treated red iron oxide (Note 5) | 4 |
| 11. Silicone treated yellow iron oxide (Note 5) | 10 |
| 12. Silicone-treated black iron oxide (Note 5) | 1 |
| 13. Acrylic silicone resin solution (Note 6) | 20 |
| 14. 1,3-Butylene glycol | 50 |
| 15. Xanthan gum (Note 7) | 50 |
| 16. Sodium citrate | 2 |
| 17. Sodium chloride | 5 |
| 18. Preservative | appropriate amount |
| 19. Fragrance | appropriate amount |
| 20. Purified water | 320 |

(Note 1)
KSG-210 manufactured by Shin-Etsu Chemical Co., Ltd.
(Note 2)
KSG-15 manufactured by Shin-Etsu Chemical Co., Ltd.
(Note 3)
KF-6028P manufactured by Shin-Etsu Chemical Co., Ltd.
(Note 4)
Product of 6 mm$^2$/sec (25° C.)
(Note 5)
Surface treated with KF-9909 manufactured by Shin-Etsu Chemical Co., Ltd.
(Note 6)
KP-575 manufactured by Shin-Etsu Chemical Co., Ltd. appropriate amount
(Note 7)
Aqueous solution of 20 g/kg.

Example 18

(Manufacture of Sunscreen Cream)

A sunscreen cream was produced in order to confirm the UV-blocking ability of the pigment of the present invention. The ingredient 7 below was added to a part of ingredient 5 to obtain a uniform mixture, and ingredients 8 and 9 were added and dispersed therein using a bead mill (step A). Separately, ingredients 1 to 4, the rest of ingredient 5, and ingredient 6 were uniformly mixed (step B). Further separately, ingredients 10 to 12, and ingredient 14 were dispersed using a stirrer until the resulting mixture became visually uniform (step C). Next, the mixture obtained in step C was added to the mixture obtained in step B to emulsify, and the dispersion obtained in step A and ingredient 13 were added thereto to obtain a sunscreen cream (step D).

It was confirmed that the obtained sunscreen cream had a high UV-blocking ability, did not cause white cast when applied to the skin, provided a finish that looked like the natural bare skin, did not feel granular when applied to the skin, and had good lubricity.

| (Ingredients) | compound ratio (g/kg) |
|---|---|
| 1. Crosslinked polyether-modified silicone (Note 1) | 30 |
| 2. Crosslinked dimethylpolysiloxane (Note 2) | 20 |
| 3. Alkyl-modified, branched polyether-modified silicone (Note 3) | 10 |
| 4. Neopentyl glycol dioctanoate | 50 |
| 5. Decamethylcyclopentasiloxane | 175 |
| 6. Octyl methoxycinnamate | 60 |
| 7. Acrylic silicone resin solution (Note 4) | 100 |
| 8. Caprylyl silane-treated zinc oxide fine particle (Note 5) | 200 |
| 9. Caprylyl silane-treated pigment described in Example 2 (Note 5) | 30 |
| 10. 1,3-Butylene glycol | 20 |
| 11. Sodium citrate | 2 |
| 12. Sodium chloride | 5 |
| 13. Fragrance | appropriate amount |
| 14. Purified water | 298 |

(Note 1)
KSG-240 manufactured by Shin-Etsu Chemical Co., Ltd.
(Note 2)
KSG-15 manufactured by Shin-Etsu Chemical Co., Ltd.
(Note 3)
KF-6038 manufactured by Shin-Etsu Chemical Co., Ltd.
(Note 4)
KP-575 manufactured by Shin-Etsu Chemical Co., Ltd.
(Note 5)
Surface treated with AES-3083 manufactured by Shin-Etsu Chemical Co., Ltd.

Example 19

(Manufacture of Film Composition)

A film composition containing the pigment of the present invention was produced. A part of ingredient 3 was added to ingredient 1, and dispersed therein using a bead mill (step A). Ingredient 2 and the rest of ingredient 3 were mixed, heated, and stirred at 95° C. for 10 minutes (step B). The dispersed solution obtained in step A was added, and after stirring for 5 minutes, the heating was ended. The mixture was poured into a mold (step C). The resultant was dried to obtain a film composition (step D).

When the obtained film composition was held up to sunlight, it was confirmed that the transmitted light had a significantly large ratio of light in the warm color range, and so the film composition had a warm color light-transmitting effect.

| (Ingredients) | compound ratio (g/kg) |
|---|---|
| 1. Pigment described in Example 4 | 100 |
| 2. Polyvinyl alcohol (Note 1) | 100 |
| 3. Purified water | 800 |

(Note 1)
Polyvinyl alcohol 500 manufactured by Kishida Chemical Co., Ltd.

Example 20

(Manufacture of Resin Composition)

A resin composition containing the pigment of the present invention was produced. Ingredient 1 was distilled and then bubbled with nitrogen for 30 minutes (step A). Ingredient 5 and ingredient 6 were mixed and dispersed using a bead mill (step B). The liquid obtained in step A and ingredients 2 to 4 were added to ingredient 7, and the mixture was heated while stirring. 5 minutes after reaching 65° C., the dispersion obtained in step B was added thereto, and stirring was continued while keeping the temperature at 65° C. (step C). After 10 hours, ingredient 8 was added to neutralize the mixture (step D), which was then filtered and washed to obtain a resin composition (step E).

When the obtained resin composition was held up to sunlight, it was confirmed that the transmitted light had a significantly large ratio of light in the warm color range, and so the resin composition had a warm color light-transmitting effect.

| (Ingredients) | compound ratio (g/kg) |
|---|---|
| 1. Methyl methacrylate | 600 |
| 2. Azoisobutyl nitrile | 0.3 |
| 3. Sodium chloride | 1 |
| 4. Calcium phosphate | 6 |
| 5. Methylhydrogenpolysiloxane surface-treated pigment described in Example 4 | 200 |
| 6. Toluene | 140 |
| 7. Purified water | appropriate amount |
| 8. Hydrochloric acid | appropriate amount |

Example 21

(Manufacture of Paint)

A paint containing the pigment of the present invention was produced. Ingredients 1 to 4 were mixed using a mixer for 30 or more and 120 minutes or less (step A), and then dispersed for 24 hours using a bead mill (step B).

When the obtained paint was applied to a transparent glass substrate and held up to light, it was confirmed that the transmitted light had a significantly large ratio of light in the warm color range, and so the paint had a warm color light-transmitting effect.

| (Ingredients) | compound ratio (g/kg) |
|---|---|
| 1. Acrylic resin | 300 |
| 2. Methylhydrogenpolysiloxane surface-treated pigment described in Example 4 | 300 |
| 3. Toluene | 200 |
| 4. Isophorone | 200 |

Example 22

(Manufacture of Ink)

An ink containing the pigment of the present invention was produced. The ingredients 1 to 4 below were mixed using a mixer for 30 or more and 120 minutes or less (step A), and then dispersed for 24 hours using a bead mill (step B).

When the obtained ink was applied to a glass plate and held up to light, it was confirmed that the transmitted light had a significantly large ratio of light in the warm color range, and so the ink had a warm color light-transmitting effect.

| (Ingredients) | compound ratio (g/kg) |
|---|---|
| 1. Acrylic resin | 75 |
| 2. Methylhydrogenpolysiloxane surface-treated pigment described in Example 4 | 495 |
| 3. Methylcyclohexane | 400 |
| 4. Dispersant (Note 1) | 10 |
| 5. Gelling agent (Note 2) | 20 |

(Note 1)
Homogenol (registered trademark) L-18 manufactured by Kao Corporation
(Note 2)
Organite (registered trademark)-T manufactured by Nihon Yuukinendo Co., Ltd.

The invention claimed is:

1. A pigment composed of particles comprising a calcium-titanium composite oxide as a main component, wherein a lattice constant a of the pigment is in a range of 5.4700 Å or more and 5.5100 Å or less,
   wherein, when the pigment is measured in X-ray diffractometry, and when a height of a diffraction line of a (1 2 1) plane appearing in a range of a diffraction angle of 32.50° or more and 33.50° or less is defined as 100.0, a height of a diffraction line of a (2 0 2) plane appearing in a range of a diffraction angle of 46.75° or more and 47.75° or less is 50.0 or less.

2. The pigment according to claim 1, wherein the calcium-titanium composite oxide is a calcium-titanium composite oxide having an orthorhombic crystal system.

3. The pigment according to claim 1, wherein the pigment has a specific surface area of 3.0 m²/g or more.

4. The pigment according to claim 1, wherein, when the pigment is measured in X-ray diffractometry, and when an integrated diffraction intensity of a (1 2 1) plane appearing in a range of a diffraction angle of 32.50° or more and 33.50° or less is defined as 100.0, a diffraction line having an integrated diffraction intensity greater than 12.00 does not appear in a range of a diffraction angle of 24.75° or more and 28.00° or less.

5. The pigment according to claim 1, wherein a coating layer of an inorganic substance and/or an organic substance is present on at least a part of a surface of the particles.

6. The pigment according to claim 1, wherein the particles have an approximately spherical shape.

7. The pigment according to claim 1, wherein the particles have a rectangular parallelepiped shape.

8. The pigment according to claim 1, wherein a crystallite size of the particles is in a range of 250 Å or more and 600 Å or less.

9. A cosmetic comprising the pigment according to claim 1.

10. A film composition comprising the pigment according to claim 1.

11. A resin composition comprising the pigment according to claim 1.

12. A paint comprising the pigment according to claim 1.

13. An ink comprising the pigment according to claim 1.

* * * * *